(12) United States Patent
Sakai et al.

(10) Patent No.: US 8,440,260 B2
(45) Date of Patent: May 14, 2013

(54) DIRUTHENIUM COMPLEX, AND MATERIAL AND METHOD FOR CHEMICAL VAPOR DEPOSITION

(75) Inventors: Tatsuya Sakai, Tokyo (JP); Sanshiro Komiya, Fuchu (JP); Naofumi Nomura, Fuchu (JP)

(73) Assignee: JSR Corporation, Tokyo (JP)

( * ) Notice: Subject to any disclaimer, the term of this patent is extended or adjusted under 35 U.S.C. 154(b) by 209 days.

(21) Appl. No.: 12/933,127

(22) PCT Filed: Sep. 4, 2008

(86) PCT No.: PCT/JP2008/066364
§ 371 (c)(1),
(2), (4) Date: Dec. 16, 2010

(87) PCT Pub. No.: WO2009/116191
PCT Pub. Date: Sep. 24, 2009

(65) Prior Publication Data
US 2011/0129602 A1 Jun. 2, 2011

(30) Foreign Application Priority Data
Mar. 17, 2008 (JP) ................................. 2008-068102

(51) Int. Cl.
*C23C 16/00* (2006.01)
*C07F 15/00* (2006.01)

(52) U.S. Cl.
USPC .................. 427/248.1; 427/250; 556/136

(58) Field of Classification Search .................. 556/136; 427/248.1, 250
See application file for complete search history.

(56) References Cited

U.S. PATENT DOCUMENTS

| | | | |
|---|---|---|---|
| 5,886,204 | A | 3/1999 | Warren et al. |
| 6,207,232 | B1 | 3/2001 | Kadokura |
| 2002/0065427 | A1 | 5/2002 | Okamoto |
| 2003/0008454 | A1 | 1/2003 | Kim |
| 2003/0088116 | A1 | 5/2003 | Kawano et al. |
| 2003/0129306 | A1 | 7/2003 | Wade et al. |
| 2003/0199169 | A1 | 10/2003 | Jun et al. |
| 2006/0024443 | A1 | 2/2006 | Sakai et al. |

FOREIGN PATENT DOCUMENTS

| | | |
|---|---|---|
| JP | 6-283438 | 10/1994 |
| JP | 10 168027 | 6/1998 |
| JP | 11-35589 | 2/1999 |
| JP | 2001-31608 | * 2/2001 |
| JP | 2002-114795 | 4/2002 |
| JP | 2002-161367 | 6/2002 |
| JP | 2002-212112 | 7/2002 |
| JP | 2002-523634 | 7/2002 |
| JP | 2003-100909 | 4/2003 |
| JP | 2003-318258 | 11/2003 |
| JP | 2003-342286 | 12/2003 |
| JP | 2006 37161 | 2/2006 |
| JP | 2006-241557 | 9/2006 |
| JP | 2006 241557 | 9/2006 |
| WO | WO 00/12776 | 3/2000 |

OTHER PUBLICATIONS

Dikarev et al., Inorganic Chemistry, vol. 45, No. 2, pp. 744-751 (2006).*

International Preliminary Report on Patentability issued dispatched Nov. 11, 2010, in International Application No. PCT/JP2008/066364.

"Electronic Parts and Materials", Nov. 2003, pp. 47-49 (with partial English translation).

Tsuyoshi Kawagoe, et al., "Novel Storage-Node Contacts with Stacked Point-Cusp Magnetron Sp-TiN Barrier for Metal-Insulator-Metal Ru/Ta$_2$O$_5$/Ru Capacitors in Gigabit Dynamic Random Access Memories", Japanese Journal of Applied Physics, vol. 43, No. 6A, 2004, pp. 3315-3319.

D. Rose, et al., "The Blue Solutions of Ruthenium (II) Chloride: a Cluster Anion †", Journal of the Chemical Society, Section A, 1970, pp. 1791-1795 (with an additional page).

Alan J. Lindsay, et al., "The Synthesis, Magnetic, Electrochemical, and Spectroscopic Properties of Diruthenium (II,II) Tetra-µ-carboxylates and their Adducts. X-Ray Structures of Ru$_2$ (O$_2$CR)$_4$L$_2$ (R = Me, L = H$_2$O or tetrahydrofuran; R = Et, L = Me$_2$CO)†", J. Chem. Soc. Dalton Trans., 1985, pp. 2321-2326 (with two additional pages).

* cited by examiner

*Primary Examiner* — Porfirio Nazario Gonzalez
(74) *Attorney, Agent, or Firm* — Oblon, Spivak, McClelland, Maier & Neustadt, L.L.P.

(57) ABSTRACT

A diruthenium complex such as tetra(µ-formato)diruthenium (II,II) or tetra(µ-formato)(dehydrate)diruthenium(II,II), a material for chemical vapor deposition which comprises the complex, and a method of forming a ruthenium film from the material by chemical vapor deposition.

16 Claims, 1 Drawing Sheet

DIRUTHENIUM COMPLEX, AND MATERIAL AND METHOD FOR CHEMICAL VAPOR DEPOSITION

This application is a 371 of PCT/JP2008/066364 filed Sep. 4, 2008. Priority to Japan 2008-068102 filed Mar. 17, 2008, is claimed.

TECHNICAL FIELD

The present invention relates to a novel diruthenium complex, and a material and a method for chemical vapor deposition.

BACKGROUND ART

Along with the high integration and miniaturization of semiconductor devices typified by DRAM (Dynamic Random Access Memory), materials for metal films and metal oxide films constituting these devices need to be changed.

Especially the improvement of a conductive metal film for use in multi-layer wiring in semiconductor devices is desired, and a shift to copper wiring having high conductivity is now under way. Although a low-dielectric material (low-k material) is used as an interlayer insulating film material for multi-layer wiring in order to enhance the conductivity of this copper wiring, there occurs a problem that an oxygen atom contained in the low-k material is easily introduced into the copper wiring to reduce its conductivity. Therefore, to prevent the movement of oxygen from the low-k material, a technology for forming a barrier film between the low-k material and the copper wring is now under study. As a material for this barrier film, which hardly takes in oxygen from a dielectric layer and can be easily processed by dry etching, a metal ruthenium film is attracting attention. Further, metal ruthenium is attracting attention to meet the requirements for the above barrier film and a film grown by plating at the same time in the Damascene film growth method for burying the above copper wring by plating (refer to Electronic Materials, November issue, pp. 47-49, November, 2003, and Jpn. J. Appl. Phys., Vol. 43, No. 6A, pp. 3315-3319, 2004).

Even in a capacitor for semiconductor devices, a metal ruthenium film is also attracting attention for its high oxidation resistance and high conductivity as an electrode material having a high dielectric constant such as alumina, tantalum pentaoxide, hafnium oxide or barium titanate•strontium (BST) (refer to JP-A 2003-100909).

Although sputtering has often been used for the formation of the above metal ruthenium film, a chemical vapor deposition method is now under study to produce a finer structure, reduce the thickness of the film and enable its mass-production (refer to JP-A2003-318258, JP-A2002-161367 and JP-A 2002-523634).

However, a metal film formed by the chemical vapor deposition method generally has bad surface morphology such as the sparse assembly state of fine crystals, and studies on the use of bis(dipivaloylmethanato)ruthenium, ruthenocene and bis(alkylcyclopentadienyl)ruthenium as materials for chemical vapor deposition are under way as means of solving the above morphology problem (refer to JP-A 06-283438, JP-A 11-35589 and JP-A 2002-114795).

When these materials for chemical vapor deposition are used in the production process, they must have high storage stability in order to stabilize the production conditions. However, existing ruthenocene and bis(alkylcyclopentadienyl)ruthenium are oxidized and deteriorated by the inclusion of air or the like in a short period of time with the result that the conductivity of the formed ruthenium film is reduced. Therefore, they have problems with storage stability and stable handling properties in air. Further, when bis(dipivaloylmethanato) ruthenium having high storage stability is used as a material for chemical vapor deposition, the formed ruthenium film contains large amounts of impurities, and a high-quality ruthenium film is not obtained. Ruthenium compounds having a carbonyl compound or a diene compound as a ligand and compounds having a ruthenium(II) valence have been studied as means of solving the above problems (refer to JP-A 2002-212112, JP-A 2003-342286 and JP-A 2006-241557). However, it is difficult to achieve storage stability for the compounds and reduce the total content of impurities remaining in the formed ruthenium film at the same time. Therefore, there still remain problems to be solved.

DISCLOSURE OF THE INVENTION

It is an object of the present invention which has been made in view of the above problems to provide a novel diruthenium complex which can provide a high-quality ruthenium film having excellent storage stability and a low total content of residual impurities, a material for chemical vapor deposition and a simple method of forming a ruthenium film from the above material for chemical vapor deposition.

Other objects and advantages of the present invention will become apparent from the following description.

According to the present invention, firstly, the above objects and advantages of the present invention are attained by a diruthenium complex represented by the following formula (1) and a material for chemical vapor deposition, comprising the complex:

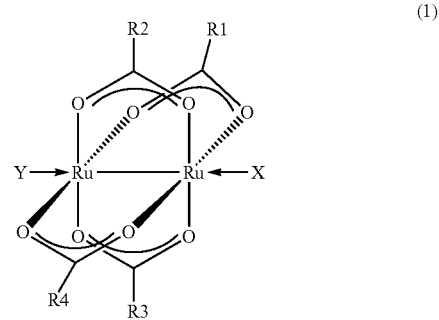

(1)

wherein R1, R2, R3 and R4 are each independently a hydrogen atom, fluorine atom, hydrocarbon group having 1 to 10 carbon atoms, halogenated hydrocarbon group having 1 to 10 carbon atoms or alkoxy group having 1 to 10 carbon atoms, and X and Y are each independently water, ketone compound having 1 to 10 carbon atoms, ether compound having 1 to 10 carbon atoms, ester compound having 1 to 10 carbon atoms or nitrile compound having 1 to 6 carbon atoms.

According to the present invention, secondly, the above objects and advantages of the present invention are attained by a diruthenium complex represented by the following formula (2) and a material for chemical vapor deposition, comprising the complex:

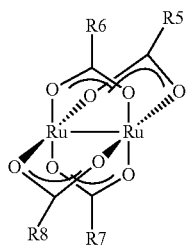

(2)

wherein R5, R6, R7 and R8 are each independently a hydrogen atom, fluorine atom, hydrocarbon group having 1 to 10 carbon atoms, halogenated hydrocarbon group having 1 to 10 carbon atoms or alkoxy group having 1 to 10 carbon atoms.

According to the present invention, thirdly, the above objects and advantages of the present invention are attained by a method of forming a ruthenium film from the above material for chemical vapor deposition by chemical vapor deposition.

BEST MODE FOR CARRYING OUT THE INVENTION

Figure 1:
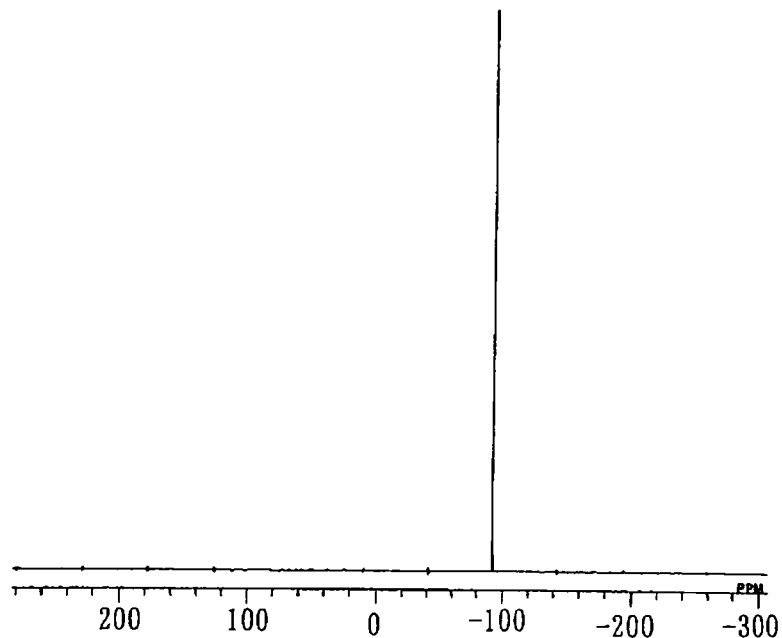
FIG. 1 is an $^{19}$F-NMR spectral diagram of tetra(μ-trifluoroacetato)di(acetone)diruthenium obtained in Example 2.

The present invention will be described in detail hereinunder.

Novel diruthenium complexes which are useful as the materials for chemical vapor deposition of the present invention are represented by the above formulas (1) and (2), respectively.

In the formula (1), R1, R2, R3 and R4 are each independently a hydrogen atom, fluorine atom, hydrocarbon group having 1 to 10 carbon atoms, halogenated hydrocarbon group having 1 to 10 carbon atoms or alkoxy group having 1 to 10 carbon atoms. The hydrocarbon group having 1 to 10 carbon atoms is preferably a hydrocarbon group having 1 to 7 carbon atoms, as exemplified by methyl group, ethyl group, n-propyl group, isopropyl group, n-butyl group, isobutyl group, t-butyl group, neopentyl group, n-hexyl group, cyclohexyl group, phenyl group, benzyl group and methylphenyl group. The halogenated hydrocarbon group having 1 to 10 carbon atoms is preferably a halogenated hydrocarbon group having 1 to 6 carbon atoms, as exemplified by chloromethyl group, dichloromethyl group, trichloromethyl group, fluoromethyl group, difluoromethyl group, trifluoromethyl group, 2.2.2-trifluoro-ethyl group, pentafluoroethyl group, perfluoropropyl group, perfluorobutyl group, perfluorohexyl group and pentafluorophenyl group. The alkoxy group having 1 to 10 carbon atoms is preferably an alkoxy group having 1 to 6 carbon atoms, as exemplified by methoxy group, ethoxy group, n-propoxy group, isopropoxy group, n-butoxy group, isobutoxy group, t-butoxy group, n-hexaoxy group and phenoxy group. Preferred examples of R1, R2, R3 and R4 include hydrogen atom, fluorine atom, methyl group, ethyl group, isopropyl group, t-butyl group, neopentyl group, trifluoromethyl group, pentafluoroethyl group, 2.2.2-trifluoro-ethyl group, perfluorohexyl group, methoxy group, ethoxy group and t-butoxy group.

In the above formula (1), X and Y are each independently water, ketone compound having 1 to 10 carbon atoms, ether compound having 1 to 10 carbon atoms, ester compound having 1 to 10 carbon atoms or nitrile compound having 1 to 6 carbon atoms. The ketone compound having 1 to 10 carbon atoms is preferably a ketone compound having 1 to 7 carbon atoms, as exemplified by acetone, 2-butanone, 3-methyl-2-butanone, 2-pentanone, pinacolone, 3-pentanone, 3-hexanone and 2-heptanone. The ether compound having 1 to 10 carbon atoms is preferably an ether compound having 1 to 6 carbon atoms, as exemplified by dimethyl ether, methyl ethyl ether, diethyl ether, tetrahydrofuran, dioxane and dipropyl ether. The ester compound having 1 to 10 carbon atoms is preferably an ester compound having 1 to 7 carbon atoms, as exemplified by methyl acetate, ethyl acetate, propyl acetate, butyl acetate, pentyl acetate, amyl acetate, methyl propionate, ethyl propionate, dimethyl carbonate and diethyl carbonate. Examples of the nitrile compound having 1 to 6 carbon atoms include acetonitrile and propionitrile. Preferred examples of X and Y include water, acetone, 2-butanone, methyl acetate, methyl propionate, dimethyl carbonate, dimethyl ether, diethyl ether, tetrahydrofuran, dioxane and acetonitrile.

In the above formula (2), R5, R6, R7 and R8 are each independently a hydrogen atom, fluorine atom, hydrocarbon group having 1 to 10 carbon atoms, halogenated hydrocarbon group having 1 to 10 carbon atoms or alkoxy group having 1 to 10 carbon atoms. The hydrocarbon group having 1 to 10 carbon atoms is preferably a hydrocarbon group having 1 to 7 carbon atoms, as exemplified by methyl group, ethyl group, n-propyl group, isopropyl group, n-butyl group, isobutyl group, t-butyl group, neopentyl group, n-hexyl group, cyclohexyl group, phenyl group, benzyl group and methylphenyl group. The halogenated hydrocarbon group having 1 to 10 carbon atoms is preferably a halogenated hydrocarbon group having 1 to 6 carbon atoms, as exemplified by chloromethyl group, dichloromethyl group, trichloromethyl group, fluoromethyl group, difluoromethyl group, trifluoromethyl group, 2.2.2-trifluoro-ethyl group, pentafluoroethyl group, perfluoropropyl group, perfluorobutyl group, perfluorohexyl group and pentafluorophenyl group. The alkoxy group having 1 to 10 carbon atoms is preferably an alkoxy group having 1 to 6 carbon atoms, as exemplified by methoxy group, ethoxy group, n-propoxy group, isopropoxy group, n-butoxy group, isobutoxy group, t-butoxy group, n-hexaoxy group and phenoxy group. Preferred examples of R5, R6, R7 and R8 include hydrogen atom, fluorine atom, methyl group, ethyl group, isopropyl group, t-butyl group, neopentyl group, monofluoromethyl group, trifluoromethyl group, pentafluoroethyl group, 2.2.2-trifluoro-ethyl group, perfluorohexyl group, methoxy group, ethoxy group and t-butoxy group.

As for the methods of synthesizing the compounds represented by the above formulas (1) and (2), refer to D. Rose and G. Wilkinson, J. Chem. Soc. (A), 1791, (1970) and A. J. Lindsay and G. Wilkinson, J. Chem. Soc. Dalton Trans., 2321, (1985).

Example of the diruthenium complex represented by the above formula (1) include tetra(μ-formato)(dihydrate)diruthenium(II,II), tetra(μ-formato)di(acetone)diruthenium(II,II), tetra(μ-formato)di(2-butanone)diruthenium(II,II), tetra(μ-formato)di(dimethylether)diruthenium(II,II), tetra(μ-formato)di(diethylether)diruthenium(II,II), tetra(μ-formato)di(tetrahydrofuran)diruthenium(II,II), tetra(μ-formato)di(dimethylcarbonato)diruthenium(II,II), tetra(μ-formato)di(methylacetato)diruthenium(II,II), tetra(μ-formato)di (methylpropionato)diruthenium(II,II), tetra(μ-formato)di(acetonitrile)diruthenium(II,II), tetra(μ-acetato)(dihydrate)diruthenium(II,II), tetra(μ-acetato)di(acetone)diruthenium(II,II), tetra(μ-acetato)di(2-butanone)diruthenium(II,II), tetra(μ-acetato)di(dimethylether)diruthenium(II,II), tetra(μ-acetato)di(diethylether)diruthenium(II,II), tetra(μ-acetato)di(tetrahydrofuran)diruthenium(II,II), tetra(μ-acetato)di(dimethylcarbonato)diruthenium(II,II), tetra(μ-acetato)di(methylacetato)diruthenium(II,II), tetra(μ-acetato)di(methylpropionato)diruthenium(II,II), tetra(μ-acetato)di(acetonitrile)diruthenium(II,II), tetra(μ-propionato)(dihydrate)diruthenium(II,II), tetra(μ-propionato)di(acetone)diruthenium(II,II), tetra(μ-propionato)di(2-butanone)diruthenium(II,II), tetra(μ-propionato)di(dimethylether)diruthenium(II,II), tetra(μ-propionato)di(diethylether)diruthenium(II,II), tetra(μ-propionato)di(tetrahydrofuran)diruthenium(II,II), tetra(μ-propionato)di(dimethylcarbonato) diruthenium(II,II), tetra(μ-propionato)di(methylpropionato) diruthenium(II,II), tetra(μ-propionato)di(acetonitrile)diruthenium(II,II), tetra(μ-monofluoroacetato)(dihydrate)diruthenium(II,II), tetra(μ-monofluoroacetato)di(acetone)diruthenium(II,II), tetra(μ-monofluoroacetato)di(2-butanone) diruthenium(II,II), tetra(μ-monofluoroacetato)di(dimethylether) diruthenium(II,II), tetra(μ-monofluoroacetato)di(diethylether) diruthenium(II,II), tetra(μ-monofluoroacetato) di(tetrahydrofuran)diruthenium(II,II), tetra(μ-monofluoroacetato)di(methylcarbonato) diruthenium(II,II), tetra(μ-monofluoroacetato)(dimethylmonofluoroacetato) diruthenium(II,II), tetra(μ-monofluoroacetato)di(acetonitrile) diruthenium(II,II), tetra(μ-trifluoromethylacetato)(dihydrate) diruthenium(II,II), tetra(μ-trifluoromethylacetato)di(acetone) diruthenium(II,II), tetra(μ-trifluoromethylacetato)di(2-butanone) diruthenium(II,II), tetra(μ-trifluoromethylacetato)di(dimethylether) diruthenium(II,II), tetra(μ-trifluoromethylacetato)di(diethylether) diruthenium(II,II), tetra(μ-trifluoromethylacetato)di(tetrahydrofuran) diruthenium(II,II), tetra(μ-trifluoromethylacetato)di(dimethylcarbonato) diruthenium(II,II), tetra(μ-trifluoromethylacetato) (dimethyltrifluoromethylacetato) diruthenium(II,II), tetra(μ-trifluoromethylacetato)di(acetonitrile) diruthenium(II,II), tetra(μ-tetrafluoroethylacetato)(dihydrate) diruthenium(II,II), tetra(μ-tetrafluoroethylacetato)di(acetone) diruthenium(II,II), tetra(μ-tetrafluoroethylacetato)di(2-butanone) diruthenium(II,II), tetra(μ-tetrafluoroethylacetato)di(dimethylether) diruthenium(II,II), tetra(μ-tetrafluoroethylacetato)di(diethylether) diruthenium(II,II), tetra(μ-tetrafluoroethylacetato)di(tetrahydrofuran) diruthenium(II,II), tetra(μ-tetrafluoroethylacetato)di(dimethylcarbonato) diruthenium(II,II), tetra(μ-tetrafluoroethylacetato)(dimethyltetrafluoroethylacetato)diruthenium(II,II), tetra(μ-tetrafluoroethylacetato)di(acetonitrile) diruthenium(II,II), tetra(μ-methoxyacetato)(dihydrate)diruthenium(II,II), tetra(μ-methoxyacetato)di(acetone)diruthenium(II,II), tetra(μ-methoxyacetato)di(2-butanone)diruthenium(II,II), tetra(μ-methoxyacetato)di(dimethylether) diruthenium(II,II), tetra(μ-methoxyacetato)di(diethylether)diruthenium(II,II), tetra(μ-methoxyacetato)di(tetrahydrofuran) diruthenium(II,II), tetra(μ-methoxyacetato)di(dimethylcarbonato) diruthenium(II,II), tetra(μ-methoxyacetato)(dimethylmethoxyacetato) diruthenium(II,II), tetra(μ-methoxyacetato)di(acetonitrile)diruthenium(II,II), tetra(μ-ethoxyacetato)(dihydrate)diruthenium(II,II), tetra(μ-ethoxyacetato)di(acetone)diruthenium(II,II), tetra(μ-ethoxyacetato)di(2-butanone)diruthenium(II,II), tetra(μ-ethoxyacetato)di(dimethylether) diruthenium(II,II), tetra(μ-ethoxyacetato)di(diethylether)diruthenium(II,II), tetra(μ-ethoxyacetato)di(tetrahydrofuran) diruthenium(II,II), tetra(μ-ethoxyacetato)di(dimethylcarbonato) diruthenium(II,II), tetra(μ-ethoxyacetato)(dimethylethoxyacetato) diruthenium(II,II) and tetra(μ-ethoxyacetato)di(acetonitrile) diruthenium(II,II).

Out of these, preferred are tetra(μ-formato)di(acetone) diruthenium(II,II), tetra(μ-formato)di(diethylether)diruthenium(II,II), tetra(μ-formato)di(tetrahydrofuran)diruthenium(II,II), tetra(μ-formato)di(acetonitrile)diruthenium(II,II), tetra(μ-acetato)di(acetone)diruthenium(II,II), tetra(μacetato)di(diethylether)diruthenium(II,II), tetra(μacetato)di(tetrahydrofuran)diruthenium(II,II), tetra(μacetato)di(acetonitrile) diruthenium(II,II), tetra(μ-propionato)di(acetone) diruthenium(II,II), tetra(μ-propionato)di(tetrahydrofuran) diruthenium(II,II), tetra(μ-trifluoromethylacetato)di(acetone) diruthenium(II,II), tetra(μ-trifluoromethylacetato)di(diethylether) diruthenium(II,II), tetra(μ-trifluoromethylacetato)di(tetrahydrofuran) diruthenium(II,II), tetra(μ-trifluoromethylacetato)di(acetonitrile) diruthenium(II,II), tetra(μ-tetrafluoroethylacetato)di(acetone) diruthenium(II,II), tetra(μ-tetrafluoroethylacetato)di(diethylether) diruthenium(II,II), tetra(μ-tetrafluoroethylacetato)di(tetrahydrofuran) diruthenium(II,II), tetra(μ-tetrafluoroethylacetato)di(acetonitrile) diruthenium(II,II), tetra(μ-methoxyacetato)di(acetone)diruthenium(II,II), tetra(μ-methoxyacetato)di(tetrahydrofuran) diruthenium(II,II) and tetra(μ-methoxyacetato)di(acetonitrile) diruthenium(II,II).

Examples of the diruthenium complex represented by the above formula (2) include tetra(μ-formato)diruthenium(II,II), tetra(μ-acetato)diruthenium(II,II), tetra(μ-propionato)diruthenium(II,II), tetra(μ-monofluoroacetato)diruthenium(II,II), tetra(μ-trifluoromethylacetato)diruthenium(II,II), tetra(μ-pentafluoroethylacetato)diruthenium(II,II), tetra(μ-methoxyacetato)diruthenium(II,II) and tetra(μ-ethoxyacetato)diruthenium(II,II).

Out of these, preferred are tetra(μ-formato)diruthenium(II,II), tetra(μ-acetato) diruthenium(II,II), tetra(μ-trifluoromethylacetato)diruthenium(II,II), tetra(μ-pentafluoroethylacetato)diruthenium(II,II) and tetra(μ-methoxyacetato) diruthenium(II,II).

These compounds may be used alone or in combination of two or more as a material for chemical vapor deposition. It is preferred that one compound should be used alone as a material for chemical vapor deposition.

The chemical vapor deposition method of the present invention uses the above material for chemical vapor deposition.

As the chemical vapor deposition method of the present invention, a method known per se may be used except that the above material for chemical vapor deposition is used and can be carried out as follows, for example.

The method comprises (1) the step of gasifying the material for chemical vapor deposition of the present invention and (2) the step of heating the obtained gas to thermally decompose it so as to deposit ruthenium on a substrate. In the above step (1), even when the decomposition of the material for chemical vapor deposition of the present invention occurs, the effect of the present invention is not thereby diminished.

As the substrate which may be used herein, a suitable material such as glass, silicon semiconductor, quartz, metal, metal oxide or synthetic resin may be used but a material which can withstand a thermal decomposition temperature in the step of thermally decomposing a ruthenium compound is preferred.

In the above step (1), the temperature for gasifying the ruthenium compound is preferably 100 to 350° C., more preferably 120 to 300° C.

In the above step (2), the temperature for thermally decomposing the ruthenium compound is preferably 180 to 450° C. more preferably 200 to 400° C., much more preferably 250 to 400° C.

The chemical vapor deposition method of the present invention may be carried out in the presence or absence of an inert gas or in the presence or absence of a reducing gas. It may also be carried out in the presence of both an inert gas and a reducing gas. Examples of the inert gas include nitrogen, argon and helium. Examples of the reducing gas include hydrogen and ammonia. It is particularly preferred that the reducing gas should be present in order to reduce the total content of impurities in the formed ruthenium film. When the reducing gas is made present, the amount of the reducing gas in the atmosphere is preferably 1 to 70 mol %, more preferably 3 to 40 mol %.

The chemical vapor deposition method of the present invention may be carried out in the presence of an oxidizing gas. Examples of the oxidizing gas include oxygen, carbon monoxide and nitrous oxide.

The chemical vapor deposition method of the present invention may be carried out under increased pressure, normal pressure or reduced pressure. The chemical vapor deposition method is carried out preferably under normal pressure or reduced pressure, more preferably under a pressure of not more than 15,000 Pa.

The diruthenium complex and the material for chemical vapor deposition of the present invention have such high storage stability that their deterioration, for example, oxidation hardly occurs when they are stored in air. When they are kept in a commercially available closed vessel for laboratory use in a cool and dark space, the deterioration of these materials does not occur for about 15 days without using an inert atmosphere in the vessel.

The ruthenium film obtained as described above has excellent storage stability, high purity and high electric conductivity as obvious from Examples which will be described hereinafter and can be advantageously used as a barrier film for wiring electrodes, a film grown by plating or a capacitor electrode.

EXAMPLES

The following examples are provided to further illustrate the present invention.

Example 1

Synthesis of tetra(μ-acetato)diruthenium(II,II)

2.0210 g of ruthenium trichloride·trihydrate, 0.0138 g of an Adams oxidation platinum catalyst and 25 mL of methanol were stirred in an autoclave under a hydrogen pressure of 6 atm for 3 hours to obtain a blue solution. After the end of stirring, the resulting solution was filtered and transferred to a Schlenk flask whose inside had been substituted by nitrogen, 2.3580 g of lithium acetate was added, and the resulting mixture was heated to reflux for 18 hours. After the end of the reflux, thermal filtration was carried out, and the filtrate was washed with methanol 3 times and vacuum dried at 80° C. to obtain 0.9207 g of tetra(μ-acetato)diruthenium as a brown powder. The yield was 54%.

When the elemental analysis of the obtained solid was carried out, the solid had a carbon content of 21.91% and a hydrogen content of 2.70%. As for the theoretical values of tetra(μ-acetato)diruthenium, the content of carbon was 21.92% and the content of hydrogen was 2.76%.

IR (KBr, cm$^{-1}$): 2936 vw, 1556 vs, 1444 vs, 1352 s, 1046 m, 944 w, 691 s, 621 w, 581 w.

Example 2

Synthesis of tetra(μ-trifluoroacetato)di(acetone)diruthenium(II,II)

0.9059 g of tetra(μ-acetato)diruthenium, 1.696 g of sodium trifluoroacetate, 28 mL of trifluoroacetic acid and 4 mL of trifluoroacetic anhydride were fed to a Schlenk flask whose inside had been substituted by nitrogen, and the resulting mixture was heated to reflux for 3 days. After the end of the reflux, filtration was carried out to obtain a cardinal solution. The solvent was distilled off in a vacuum, and extraction was carried out with ether. Vacuum distillation was carried out again, recrystallization was carried out by using acetone, and the obtained product was washed with hexane and vacuum dried to obtain 1.3517 g of tetra(μ-trifluoroacetato)di(acetone)diruthenium as a purple-red solid. The yield was 65%.

When the elemental analysis of the obtained solid was carried out, the solid had a carbon content of 22.19% and a hydrogen content of 1.62%. As for the theoretical values of tetra(μ-trifluoroacetato)di(acetone)diruthenium, the content of carbon was 21.83% and the content of hydrogen was 1.57%.

$^{19}$F-NMR (CDCl$_3$) δ−91.68 (s, CCF$_3$), FIG. 1.

IR (KBr, cm$^{-1}$): 2928 w, 2918 w, 1681 s, 1644 s, 1195 vs, 1167 s, 859 m, 777 m, 736 s, 552 m, 529 m.

Example 3

Synthesis of tetra(μ-pentafluoropropionato)di(acetone)diruthenium(II,II)

100.4 mg of tetra(μ-acetato)diruthenium, 194.1 mg of sodium pentafluoropropionate, 3.6 mL of pentafluoropropionic acid and 0.4 mL of pentafluoropropionic anhydride were fed to a Schlenk flask whose inside had been substituted by nitrogen, and the resulting mixture was heated to reflux for 3 days. After the end of the reflux, filtration was carried out to obtain a cardinal solution. The solvent was distilled off in a vacuum, and extraction was carried out with ether. Vacuum distillation was carried out again, recrystallization was carried out by using acetone/hexane, and the obtained product was washed with hexane and vacuum dried to obtain 122.4 mg of tetra(μ-pentafluoropropionato)di(acetone)diruthenium as a purple-red solid. The yield was 55%.

When the elemental analysis of the obtained solid was carried out, the solid had a carbon content of 22.56% and a hydrogen content of 1.53%. As for the theoretical values of tetra(μ-pentafluoropropionato)di(acetone)diruthenium, the content of carbon was 22.28% and the content of hydrogen was 1.25%.

Figure 2:
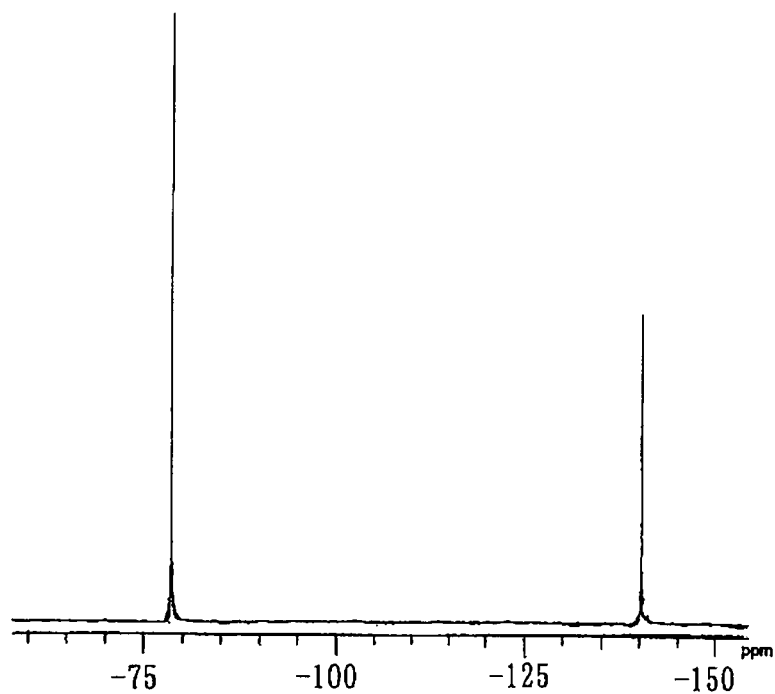
FIG. 2 is an $^{19}$F-NMR spectral diagram of tetra(μ-pentafluoropropionato)di(acetone)diruthenium obtained in Example 3.

$^{19}$F-NMR (CDCl$_3$) δ−78.62 (s, 12F, CF$_3$), −140.21 (s, 8F, CF$_2$). FIG. 2.

IR (KBr, cm$^{-1}$): 2932 w, 2866 w, 1683 s, 1670 sh, 1639 s, 1438 m, 1333 m, 1227 s, 1192 sh, 1165 s, 1036 s, 832 m, 737 m, 553 m.

In the following examples, the resistivity was measured with the RT-80/RG-80 probe resistivity measurement instrument of Napson Co., Ltd. The film thickness and density were measured with the X'Pert MRD grazing incident X-ray analyzer of Philips Co., Ltd. The ESCA spectrum was measured with the JPS80 of JEOL Ltd. Adhesion was evaluated by the cross-cut tape method in accordance with JIS K-5400.

Example 4

(1) 0.05 g of tetra(μ-acetato)diruthenium(II,II) obtained in Example 1 was weighed, put into a quartz boat type vessel in a nitrogen gas atmosphere and set in a quartz reactor. A silicon wafer having a thermally oxidized film was placed near the downstream direction of a gas stream in the reactor, and a nitrogen gas was let flow into the reactor at a rate of 300 mL/min at room temperature for 20 minutes. Thereafter, a nitrogen gas was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a nitrogen gas was let flow at a rate of 200 mL/min under a pressure of 101.3 kPa, and the temperature of reactor was raised to 420° C. and kept at that temperature for 1 hour, a film having metallic luster was obtained on the substrate. The thickness of this film was 920 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 35 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-acetato)diruthenium(II,II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-acetato)diruthenium(II,II) did not change. When the vessel was returned to room temperature, the inside of the vessel was substituted by dry nitrogen and film formation was carried out in the same manner as in (1) above, a film having metallic luster was obtained on the substrate. The thickness of this film was 920 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 35 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Example 5

(1) 0.05 g of tetra(μ-acetato)diruthenium(II,II) obtained in Example 1 was weighed, put into a quartz boat type vessel in a nitrogen gas atmosphere and set in a quartz reactor. A silicon wafer having a thermally oxidized film was placed near the downstream direction of a gas stream in the reactor, and a hydrogen/nitrogen mixed gas (hydrogen content of 3 vol %) was let flow into the reactor at a rate of 300 mL/min at room temperature for 20 minutes. Thereafter, a hydrogen/nitrogen mixed gas (hydrogen content of 3 vol %) was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a hydrogen/nitrogen mixed gas (hydrogen content of 3 vol %) was let flow at a rate of 200 mL/min under a pressure of 101.3 kPa, and the temperature of the reactor was raised to 420° C. and kept at that temperature for 1 hour, a film having metallic luster was obtained on the substrate. The thickness of this film was 900 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 28 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-acetato)diruthenium(II,II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-acetato)diruthenium(II,II) did not change. When the vessel was returned to room temperature, the inside of the vessel was substituted by dry nitrogen, and film formation was carried out in the same manner as in (1) above, a film having metallic luster was obtained on the substrate. The thickness of this film was 900 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 28 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Example 6

(1) 0.05 g of tetra(μ-trifluoroacetato)di(acetone)diruthenium(II,II) obtained in Example 2 was weighed, put into a quartz boat type vessel in a nitrogen gas atmosphere and set in a quartz reactor. A silicon wafer having a thermally oxidized film was placed near the downstream direction of a gas stream in the reactor, and a nitrogen gas was let flow into the reactor at a rate of 300 mL/min at room temperature for 20 minutes. Thereafter, a nitrogen gas was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a nitrogen gas was let flow at a rate of 200 mL/min under a pressure of 101.3 kPa, and the temperature of reactor was raised to 400° C. and kept at that temperature for 1 hour, a film having metallic luster was obtained on the substrate. The thickness of this film was 900 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 21 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-trifluoroacetato)di(acetone)diruthenium (II,II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-trifluoroacetato)di(acetone)diruthenium(II,II) did not change. When the vessel was returned to room temperature, the inside of the vessel was substituted by dry nitrogen, and film formation was carried out in the same manner as in (1) above, a film having metallic luster was obtained on the substrate. The thickness of this film was 900 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 21 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Example 7

(1) 0.05 g of tetra(μ-trifluoroacetato)di(acetone)diruthenium (II,II) obtained in Example 2 was weighed, put into a quartz boat type vessel in a nitrogen gas atmosphere and set in a quartz reactor. A silicon wafer having a thermally oxidized film was placed near the downstream direction of a gas stream in the reactor, and a hydrogen/nitrogen mixed gas (hydrogen content of 3 vol %) was let flow into the reactor at a rate of 300 mL/min at room temperature for 20 minutes. Thereafter, a hydrogen/nitrogen mixed gas (hydrogen content of 3 vol %) was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a hydrogen/nitrogen mixed gas (hydrogen content of 3 vol %) was let flow at a rate of 200 mL/min under a pressure of 101.3 kPa, and the temperature of the reactor was raised to 400° C. and kept at that temperature for 1 hour, a film having metallic luster was obtained on the substrate. The thickness of this film was 870 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 18 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-trifluoroacetato)di(acetone)diruthenium (II,II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-trifluoroacetato)di(acetone)diruthenium(II,II) did not change. When the vessel was returned to room temperature, the inside of the vessel was substituted by dry nitrogen, and film formation was carried out in the same manner as in (1) above, a film having metallic luster was obtained on the substrate. The thickness of this film was 870 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 18 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Example 8

(1) 0.05 g of tetra(μ-pentafluoropropionato)di(acetone)diruthenium(II, II) obtained in Example 3 was weighed, put into a quartz boat type vessel in a nitrogen gas atmosphere and set in a quartz reactor. A silicon wafer having a thermally oxidized film was placed near the downstream direction of a gas stream in the reactor, and a nitrogen gas was let flow into the reactor at a rate of 300 mL/min at room temperature for 20 minutes. Thereafter, a nitrogen gas was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a nitrogen gas was let flow at a rate of 200 mL/min under a pressure of 101.3 kPa, and the temperature of reactor was raised to 400° C. and kept at that temperature for 1 hour, a film having metallic luster was obtained on the substrate. The thickness of this film was 600 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 16 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-pentafluoropropionato)di(acetone)diruthenium(II, II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-pentafluoropropionato)di(acetone)diruthenium(II, II) did not change. When the vessel was returned to room temperature, the inside of the vessel was substituted by dry nitrogen, and film formation was carried out in the same manner as in (1) above, a film having metallic luster was obtained on the substrate. The thickness of this film was 600 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 16 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Example 9

(1) 0.05 g of tetra(μ-pentafluoropropionato)di(acetone)diruthenium(II, II) obtained in Example 3 was weighed, put into a quartz boat type vessel in a nitrogen gas atmosphere and set in a quartz reactor. A silicon wafer having a thermally oxidized film was placed near the downstream direction of a gas stream in the reactor, and a hydrogen/nitrogen mixed gas (hydrogen content of 3 vol %) was let flow into the reactor at a rate of 300 mL/min at room temperature for 20 minutes. Thereafter, a hydrogen/nitrogen mixed gas (hydrogen content of 3 vol %) was let flow into the reactor at a rate of 100 mL/min, the inside pressure of the system was reduced to 13 Pa, and the reactor was heated at 400° C. for 15 minutes. Mist was generated from the boat type vessel, and a deposit was seen on a quartz substrate placed near the vessel. After the generation of mist ended, when depressurization was stopped, a nitrogen gas was introduced into the system to restore the initial pressure, a hydrogen/nitrogen mixed gas (hydrogen content of 3 vol %) was let flow at a rate of 200 mL/min under a pressure of 101.3 kPa, and the temperature of the reactor was raised to 400° C. and kept at that temperature for 1 hour, a film having metallic luster was obtained on the substrate. The thickness of this film was 570 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 21 μΩcm. The density of this film was 12.0 g/cm$^3$. When adhesion between the ruthenium film formed herein and the substrate was evaluated by the cross-cut tape method, the peeling of the ruthenium film from the substrate was not seen at all.

(2) As for the confirmation of storage stability, a heating and acceleration test was carried out to investigate deterioration by air. 1 g of tetra(μ-pentafluoropropionato)di(acetone)diruthenium(II, II) was put into a quartz 3-necked flask having a capacity of 50 mL, the whole vessel was heated at 50° C., and then air was let flow into the vessel at a rate of 3 L/min under normal pressure for 3 hours. The appearance of tetra(μ-pentafluoropropionato)di(acetone) diruthenium(II,II) did not change. When the vessel was returned to room temperature, the inside of the vessel was substituted by dry nitrogen, and film formation was carried out in the same manner as in (1) above, a film having metallic luster was obtained on the substrate. The thickness of this film was 570 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 21 μΩcm. The density of this film was 12.0 g/cm$^3$. When adhesion between the ruthenium film formed herein and the substrate was evaluated by the cross-cut tape method, the peeling of the ruthenium film from the substrate was not seen at all, and the deterioration of the ruthenium metal film by an air exposure heating test was not observed.

Comparative Example 1

(1) 0.01 g of commercially available bis(ethylcyclopentadienyl)ruthenium was weighed, put into a quartz boat type vessel in a nitrogen gas atmosphere and set in a quartz reactor. A quartz substrate was placed near the downstream direction of a gas stream in the reactor, and an oxygen/nitrogen mixed gas (oxygen content of 5 vol %) was let flow into the reactor at a rate of 250 mL/min at room temperature for 60 minutes. Thereafter, an oxygen/nitrogen mixed gas (oxygen content of 5 vol %) was let flow into the reactor at a rate of 20 mL/min, the inside pressure of the system was reduced to 110 Pa, and the reactor was heated at 350° C. for 30 minutes. Mist was generated from the boat type vessel, and a deposit was seen on the quartz substrate placed near the vessel. After the generation of mist ended, when depressurization was stopped, a nitrogen gas was introduced into the system to restore the initial pressure, and a nitrogen gas was let flow at a rate of 200 mL/min under a pressure of 101.3 kPa and kept flowing for 1 hour, a film having metallic luster was obtained on the substrate. The thickness of this film was 850 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was 25 μΩcm. The density of this film was 12.1 g/cm$^3$. When adhesion between the ruthenium film formed herein and the substrate was evaluated by the cross-cut tape method, the peeling of the ruthenium film from the substrate was not seen at all.

(2) A heating and acceleration test was carried out on commercially available bis(ethylcyclopentadienyl)ruthenium to investigate its deterioration by air in the same manner as in (2) of Example 1. 1 g of bis(ethylcyclopentadienyl)ruthenium was put into a quartz 3-necked flask having a capacity of 50 mL, the whole vessel was heated at 50° C., and then air was let flow into the vessel at a rate of 3 L/min under normal pressure for 3 hours. The appearance of bis(ethylcyclopentadienyl) ruthenium which was originally a light yellow transparent liquid changed to a yellow opaque liquid. When the vessel was returned to room temperature, the inside of the vessel was substituted by dry nitrogen, and film formation was carried out in the same manner as in (1) above, a film having slightly dark metallic luster was obtained on the substrate. The thickness of this film was 300 Å.

When the ESCA spectrum of this film was measured, a peak attributed to the $Ru_{3d}$ orbit was seen at 280 eV and 284 eV, and a peak derived from another element was not seen at all, whereby it was found that the film was made of metal ruthenium. When the resistivity of this ruthenium film was measured by the 4-terminal method, it was low at 78 μΩcm. The density of this film was 10.8 $g/cm^3$. When adhesion between the ruthenium film formed herein and the substrate was evaluated by the cross-cut tape method, 80 ruthenium film pieces peeled off out of 100 cross-cut ruthenium film pieces, thereby greatly deteriorating the ruthenium film. Thus, the formed ruthenium metal film formed from bis(ethylcyclopentadienyl)ruthenium was deteriorated by an air exposure heating test.

As described above, a high-quality ruthenium film having a low total content of the residual impurities and excellent long-term storage stability can be obtained from the material for chemical vapor deposition of the present invention. A ruthenium film can be formed from the material for chemical vapor deposition by a simple method.

The invention claimed is:

1. A method of forming a ruthenium film from a material comprising a diruthenium complex represented by the following formula (1) by chemical vapor deposition:

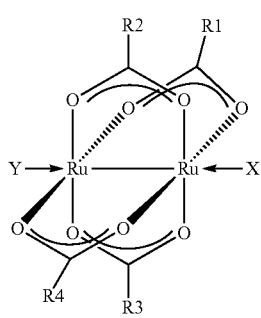

(1)

wherein R1, R2, R3 and R4 are each independently a hydrogen atom, a fluorine atom, a hydrocarbon group having 1 to 10 carbon atoms, a halogenated hydrocarbon group having 1 to 10 carbon atoms or an alkoxy group having 1 to 10 carbon atoms, and X and Y are each independently water, a ketone compound having 1 to 10 carbon atoms, an ether compound having 1 to 10 carbon atoms, an ester compound having 1 to 10 carbon atoms or a nitrile compound having 1 to 6 carbon atoms.

2. A method of forming a ruthenium film from a material comprising a diruthenium complex represented by the following formula (2) by chemical vapor deposition:

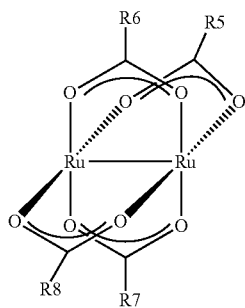

(2)

wherein R5, R6, R7 and R8 are each independently a hydrogen atom, a fluorine atom, a hydrocarbon group having 1 to 10 carbon atoms, a halogenated hydrocarbon group having 1 to 10 carbon atoms or an alkoxy group having 1 to 10 carbon atoms.

3. The method according to claim 1, comprising gasifying said material and heating the obtained gas to thermally decompose it so as to deposit ruthenium on a substrate.

4. The method according to claim 3, wherein said substrate is a glass, silicon semiconductor, quartz, metal, metal oxide or synthetic resin substrate.

5. The method according to claim 3, wherein the material is gasified at a temperature of 100 to 350° C.

6. The method according to claim 5, wherein the gas is thermally decomposed at 180 to 450° C.

7. The method according to claim 1, wherein the chemical vapor deposition is carried out in the presence of an inert gas.

8. The method according to claim 1, wherein the chemical vapor deposition is carried out in the presence of a reducing gas.

9. The method according to claim 1, wherein said material consists of a diruthenium complex represented by formula (1).

10. The method according to claim 2, comprising gasifying said material and heating the obtained gas to thermally decompose it so as to deposit ruthenium on a substrate.

11. The method according to claim 10, wherein said substrate is a glass, silicon semiconductor, quartz, metal, metal oxide or synthetic resin substrate.

12. The method according to claim 10, wherein the material is gasified at a temperature of 100 to 350° C.

13. The method according to claim 12, wherein the gas is thermally decomposed at 180 to 450° C.

14. The method according to claim 2, wherein the chemical vapor deposition is carried out in the presence of an inert gas.

15. The method according to claim 2, wherein the chemical vapor deposition is carried out in the presence of a reducing gas.

16. The method according to claim 2, wherein said material consists of a diruthenium complex represented by formula (2).

* * * * *